United States Patent [19]
Wada et al.

[11] Patent Number: 5,114,463
[45] Date of Patent: May 19, 1992

[54] PYRIMIDINE DERIVATIVES AND HERBICIDAL COMPOSITIONS CONTAINING THE SAME

[75] Inventors: Nobuhide Wada, Kakegawa; Ryo Yoshida, Shizuoka, both of Japan

[73] Assignees: Kumiai Chemical Industry Co., Ltd.; Ihara Chemical Industry Co., Ltd., both of Tokyo, Japan

[21] Appl. No.: 662,570

[22] Filed: Feb. 28, 1991

[51] Int. Cl.$^5$ .................. H01N 43/54; C07D 403/10
[52] U.S. Cl. ........................................ 71/92; 544/296
[58] Field of Search ............................ 544/296; 71/92

[56] References Cited

U.S. PATENT DOCUMENTS

| | | | |
|---|---|---|---|
| 4,248,619 | 2/1981 | Serban et al. | 71/92 |
| 4,427,437 | 1/1984 | Serban et al. | 71/92 |
| 4,889,552 | 12/1989 | Wada et al. | 71/92 |
| 4,906,285 | 3/1990 | Wada et al. | 71/92 |
| 4,985,066 | 1/1991 | Wada et al. | 71/92 |

OTHER PUBLICATIONS

Jojima et al. *Agr. Biol. Chem*, 1966, vol. 30, pp. 896–905 "Syntheses and Herbicidal Activities of Phenoxypyrimidines and Phenoxytriaznes".

*Primary Examiner*—Mukund J. Shah
*Assistant Examiner*—E. Bernhardt
*Attorney, Agent, or Firm*—Oblon, Spivak, McClelland, Maier & Neustadt

[57] ABSTRACT

A herbicidal pyrimidine derivative having the formula,

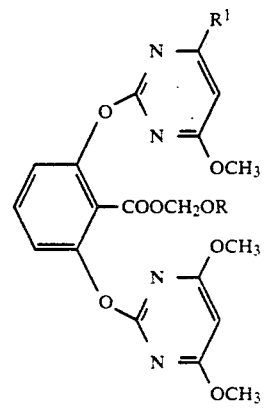

wherein R is a lower alkyl group, and $R^1$ is a lower alkoxy group, a halogen atom or a halogen-substituted lower alkoxy group.

9 Claims, No Drawings

PYRIMIDINE DERIVATIVES AND HERBICIDAL COMPOSITIONS CONTAINING THE SAME

BACKGROUND OF THE INVENTION

1. FIELD OF THE INVENTION

The present invention relates to novel pyrimidine derivatives (hereinafter referred to as "the compounds of the present invention") and to herbicidal compositions containing said pyrimidine derivatives as active ingredients, which can be applied to paddy fields, upland fields or non-agricultural fields.

2. DESCRIPTION OF THE PRIOR ART

U.S. Pat. No. 4,248,619 (Japanese Unexamined Patent Publication No. 24195/1980), U.S. Pat. No. 4,427,437 (Japanese Unexamined Patent Publication No. 55729/1979), U.S. Pat. No. 4,906,285 (Japanese Unexamined Patent Publicaiton No. 250365/1989), and Agr. Biol. Chem., Vol. 30, No. 9, p.896 (1966) disclose that 2-phenoxypyrimidine derivatives have herbicidal activities.

The above U.S. Pat. No. 4,906,285 (Japanese Unexamined Patent Publication No. 250365/1989) discloses also the herbicidal function of bispyrimidinyloxybenzoic acid derivatives. Heretofore, it has been known that the bispyrimidinyloxybenzoic acid derivatives have excellent herbicidal effect and safety. However, it is a general demand required for agricultural chemicals to reduce the scattering amount of an effective ingredient by improving the herbicidal effect.

Thus, the present inventors have found that compounds having the benzoic acid part esterified, exhibit excellent herbicidal effects against perennial weeds as well as annual weed, and at the same time, they have a high level of safety to crop plants, particularly to rice and wheat, and achieved the present invention based thereon.

SUMMARY OF THE INVENTION

An object of the present invention is to provide a novel pyrimidine derivative having the formula,

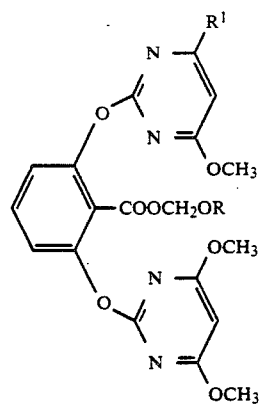

[I]

wherein R is a lower alkyl group, and $R^1$ is a lower alkoxy group, a halogen atom or a halogen-substituted lower alkoxy group, and a herbicidal composition containing said pyrimidine derivative as an active ingredient.

DETAILED DESCRIPTION OF THE INVENTION

Typical examples of the compound expressed by the general formula [I] of the present invention are listed in the following Table 1.

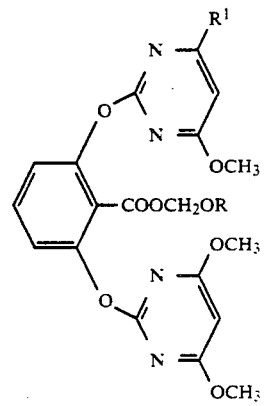

| Compound No. | R | $R^1$ | Physical Properties Refractive Index ($n_D^{20}$), or m.p. (°C.) |
|---|---|---|---|
| 1 | $CH_3$ | $OCH_3$ | 95–96 |
| 2 | $C_2H_5$ | $OCH_3$ | 102–104 |
| 3 | $CH_3$ | $OCHF_2$ | 1.5389 |
| 4 | $CH_3$ | Cl | 87–90 |

The compound of the present invention can be prepared, for example, by the following process:

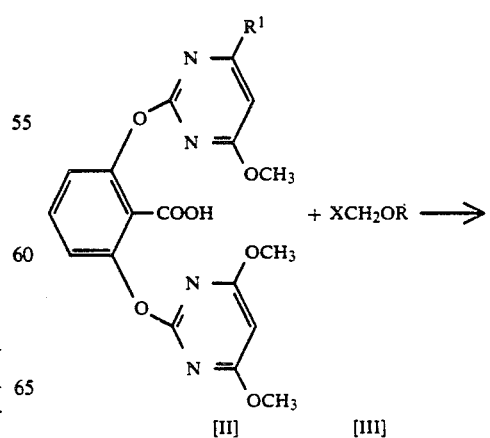

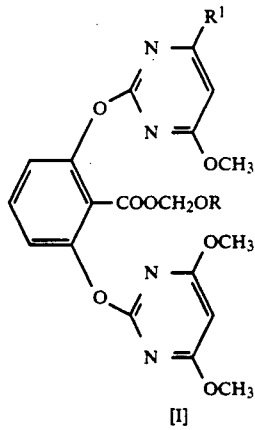

(wherein R and $R^1$ are as defined above, and X is a halogen atom).

That is, the compound of the general formula [I] of the present invention can be prepared by reacting the compound of the general formula [II] with the compound of the general formula [III] in the presence of more than equivalent amount of a base in a solvent at a temperature in the range of from room temperature to the boiling point of the solvent for from 0.5 to 48 hours. As the base, there may be employed an alkali metal such as sodium, potassium or the like; an alkali metal hydride and an alkaline earth metal hydride such as sodium hydride, potassium hydride, calcium hydride or the like; an alkali metal carbonate such as sodium carbonate, potassium carbonate or the like; and an organic amine such as triethyl amine, pyridine or the like.

As the solvent, there may be employed, a hydrocarbon solvent such as benzene, toluene, xylyne or the like; a halogenated hydrocarbon solvent such as methylene chloride, chloroform or the like; an alcohol solvent such as methanol, ethanol, 2-propanol or the like; an ether solvent such as diisopropyl ether, tetrahydrofuran, dioxane or the like; a ketone solvent such as acetone, methyl ethyl ketone or the like; an ester solvent such as methyl acetate, ethyl acetate or the like; an aprotic polar solvent such as dimethylformamide, dimethylacetamide, dimethylsulfoxide or the like, and other solvents such as acetonitrile; or combinations of these solvents.

Now, the present invention will be described in further detail with reference to Examples. However, it should be understood that the present invention is by no means restricted to such specific Examples.

EXAMPLE 1

Preparation of methoxymethyl 2,6-bis[(4,6-dimethoxypyrimidin-2-yl)oxy]benzoate (Compound No. 1)

1.5 g (3.5 mmol) of 2,6-bis[(4.6-dimethoxypyrimidin-2-yl)oxy]benzoic acid was dissolved in N,N-dimethylformamide, and 0.1 g of 60% sodium hydride was added to the resultant solution with stirring. After the generation of hydrogen ceased, 0.4 g of chloromethylmethylether was added to the solution and the resultant mixture was reacted at 100° C. for 3 hours. After completing the reaction, ice water and ethyl acetate were added to the reaction mixture, and the ethyl acetate layer was separated and washed with water. The washed ethyl acetate layer was then dried to be concentrated, and an oily product obtained thereby was subjected to column purification to obtain 1.0 g of a white crystal having a melting point of from 95° to 96° C.

EXAMPLE 2

Preparation of methoxymethyl 2-(4-difluoromethoxy-6-methoxypyrimidin-2-yl)oxy-6-(4,6-dimethoxypyrimidin-2-yl)oxybenzoate (compound No. 3)

0.9 g of (1.9 mmol) of 2-(4-difluoromethoxy-6-methoxypyrimidin-2-yl)oxy-6-(4,6-dimethoxypyrimidin-2-yl)oxybenzoic acid, 0.1 g of 60% sodium hydride and 0.2 g of chloromethylmethylether were reacted in N,N-dimethylformamide, treated and purified in the same manner as in Example 1 to obtain 0.8 g of a colorless transparent viscous liquid having a refractive index of $n_D^{20} = 1.5389$.

The herbicidal composition of the present invention comprises the pyrimidine derivative of the present invention of the general formula [I] as an effective ingredient.

When the compound of the present invention is applied as a herbicide to paddy field, upland field, fruit garden, non-agriculture land or the like, the effective ingredient may be applied in various formulations depending on its use object.

Generally, the herbicide of the present invention may be used as it is or may be formulated in various formulations which are commonly used as herbicidal compositions, such as a wettable powder, a granule, an emulsifiable concentrate or a dust by blending it with an inert liquid or solid carrier, a surfactant, a dispersing agent or an adjuvant which is commonly employed for the formulation of agricultural chemicals.

The proportion of the compound of the present invention in the formulation may vary depending upon the type of the formulation, the application method, the application site, timing, etc. Therefore, it can not generally be defined. However, it is usually from 5 to 90% by weight in a wettable powder formulation, from 5 to 80% by weight in an emulsifiable concentrate formulation, from 1 to 60% by weight in a flowable formulation, from 0.5 to 20% by weight in a granule formulation, from 5 to 40% by weight in a liquid formulaiton, from 0.5 to 10% by weight in a dust formulation and from 5 to 90% by weight in a dry flowable formulation.

As the carrier to be used for the formulation, there may be mentioned a solid carrier such as Jeeklight, talc, bentonite, clay, kaolin, diatomaceous earth, white carbon, vermiculite, slaked lime, silica sand, ammonium sulfate or urea, or a liquid carrier such as isopropyl alcohol, xylene, cyclohexanone or methyl naphthalene. As the surfactant and dispersing agent, there may be mentioned, for example, an alcohol-sulfuric acid ester, an alkylaryl sulfonate, lignin sulfonate, a polyoxyethylene glycol ether, a polyoxyethylene alkyl aryl ether or a polyoxyethylene sorbitol mono-alkylate. As the adjuvant, for example, carboxymethylcellulose, polyethylene glycol or gum arabic may be mentioned. The herbicide may be diluted to a suitable concentration before application, or may directly be applied.

The herbicide of the present invention is capable of controlling various weeds in an agricultural field such as an upland field or an orchard, or in a forest, a lawn or other non-agricultural field by soil treatment before or after the emergence of weeds or by foliage treatment. Further, the herbicide is capable of controlling various weeds in a paddy field by irrigated soil treatment before or after the emergence of weeds or by foliage treatment.

For soil treatment, the herbicide of the present invention is applied in a dose of from 0.1 g to 1 kg, preferably from 0.5 to 500 g, more preferably from 1 to 100 g of the active ingredient per 10 ares. For foliage treatment, it is diluted to a concentration of from 1 to 10,000 ppm for application. Most preferably, it is applied in a dose of from 1 to 10 g of the active ingredient per 10 ares for a paddy field, in a dose of from 5 to 50 g per 10 ares for an orchard or a lawn, and in a dose of form 10 to 100 g for a forest or a non agricultured field.

If desired, the compound of the present invention may be used in combination with insecticides, sterilizers, other herbicides, plant growth controlling agents, fertilizers or the like.

Now, typical Formulation Examples for the herbicidal composition of the present invention will be given. However, it should by understood that the present invention is by no means restricted to these specific Formulation Examples. In these Examples, "part" means "part by weight".

FORMULATION EXAMPLE 1 (wettable powder)

10 Parts of Compound No. 1, 0.5 part of Emulgen 810 (trademark, Kao Corporation), 0.5 part of Demol N (trademark, Kao Corporation), 20 parts of Kunilite 201 (trade mark, Kunimine Kogyo K.K.) and 69 parts of Jeeklite CA (trademark, Jeeklite Company Ltd.) were uniformly mixed and pulverized to obtain a wettable powder.

FORMULATION EXAMPLE 2 (wettable powder)

10 Parts of Compound No. 2, 0.5 part of Emulgen 810, 0.5 part of Demol N, 20 parts of Kunilite 201, 5 parts of Carplex 80 and 64 parts of Jeeklite CA were uniformly mixed and pulverized to obtain a wettable powder.

FORMULATION EXAMPLE 3 (emulsifiable concentrate)

30 Parts of Compound No. 3, 60 parts of equivalent amount mixture of xylene and isophorone, and 10 parts of surface active agent Sorpol 800A (trademark, Toho Kagaku Kogyo K.K.) were uniformly mixed and stirred to obtain an emulsifiable concentrate.

FORMULATION EXAMPLE 4 (granule)

10 Parts of Compound No. 4, 80 parts of a bulking agent comprising a 1:3 mixture of talc and bentonite, 5 parts of white carbon, 5 parts of surface active agent Sorpol 800A and 10 parts of water were fully kneaded to obtain a paste-like material. The paste-like material was then extruded through a sieve aperture of 0.7 mm in diameter, and the extruded product was dried and cut into pieces of 0.5 to 1 mm in length to obtain granules.

The compounds and the herbicidal compositions of the present invention are capable of effectively controlling annual weeds such as barnyardgrass (*Echinochloa crusgalli*), crabgrass (*Digitaria sanquinalis*), goosegrass (*Eleusine indica*), green foxtail (*Setaria viridis*), water foxtail (*Alopecurus aequalis*), annual bluegrass (*Poa annua*), wild oat (*Avena fatua*), italian ryegrass (*Lolium multiflorum*), smartweed (*Polygonum lapathifolium*), slender amaranth (*Amaranthus viridis*), lambsquarters (*Chenopodium album*), velvetleaf (*Abutilon theophrasti*), prickly sida (*Sida spinosa*), sicklepod (*Cassia tora*), chickweed (*Stellaria media*), morningglory (*Ipomoea spp*), common cocklebur (*Xanthium strumarium*), rice flatsedge (*Cyperus iria*), broadleaf signalgrass (*Brachiaria platyphylla*), itchgrass (*Rottoboelia exaltata*), downy brome (*Bromus tectorum*), wild buckwheat (*Polygonum convolvulus*), wild mustard (*Brassica arvensis*) and devils beggarticks (*Bidens frondasa*), and perennial weeds such as purple nutsedge (*Cyperus rotundus*), johnsongrass (*Sorghum halepense*), bermudagrass (*Cynodon dactylon*) and quackgrass (*Agropyron repens*) grown in upland fields including agricultural fields, orchards and non-agricultural fields.

Further, they are capable of effectively controlling annual weeds such as barnyardgrass (*Echinochloa crusgalli*), small flower flatsedge (*Cyperus difformis*), monochoria (*Monochoria vaginalis*), and perennial weeds such as bulrush (*Scirpus hotarui*) *Alisma canaliculatum*, *Cyperus serotinus*, *Saqittaria pyqmaea* and *Eleocharis kuroquwai*, grown in paddy fields.

On the other hand, the herbicides of the present invention are highly safe to crop plants, particularly rice, wheat, barley, corn, or the like.

These effects of the compounds and the herbicides of the present invention are equivalent to those of the conventional bispyrimidinyloxybenzoic acid derivatives and the herbicides containing the same as active ingredients, but are more superior in the application to the water surface of a paddy field as compared with those of the conventional ones.

Now, the herbicidal activities of the compounds and the herbicides of the present invention will be described with reference to Test Examples.

TEST EXAMPLE 1 (herbicidal effect test by upland field foliage treatment)

In a plastic pot filled with upland soil (surface area 120 cm$^2$), seeds of barnyardgrass (Ec), crabgrass (Di), pale smartweed (Po), slender amaranth (Am), and lambsquarters (Ch) are sown to a depth of 0.5 to 1 cm, and were cultured in a green house for 2 weeks. A predetermined amount of a wettable powder prepared in accordance with Formulation Example 1 was diluted with water, and applied by a small-sized sprayer onto the foliage in an amount of 100 l/10 ares so that the dose of the active ingredient was 400 g/10 ares. The plants were cultured in the green house, and the evaluation was conducted on the 14th day after the treatment in accordance with the standard as identified in the following Table 2-1. The test results are shown in the following Table 3.

TABLE 2-1

| Index No. | Herbicidal effect |
| --- | --- |
| 0 | Herbicidal effect: more than 0% and less than 10% |
| 1 | Herbicidal effect: at least 10% and less than 30% |
| 2 | Herbicidal effect: at least 30% and less than 50% |
| 3 | Herbicidal effect: at least 50% and less than 70% |
| 4 | Herbicidal effect: at least 70% and less than 90% |
| 5 | Herbicidal effect: at least 90% |

TABLE 2-2

| Index No. | Phytotoxicity |
| --- | --- |
| 0 | Phytotoxicity: more than 0% and less than 10% |
| 1 | Phytotoxicity: at least 10% and less than 30% |
| 2 | Phytotoxicity: at least 30% and less than 50% |
| 3 | Phytotoxicity: at least 50% and less than 70% |
| 4 | Phytotoxicity: at least 70% and less than 90% |
| 5 | Phytotoxicity: at least 90% to completely |

TABLE 2-2-continued

| Index No. | Phytotoxicity |
|---|---|
| | withered |

TABLE 3

| Compound No. | Herbicidal effect | | | | |
|---|---|---|---|---|---|
| | Ec | Di | Po | Am | Ch |
| 1 | 5 | 5 | 5 | 5 | 5 |
| 2 | 5 | 5 | 5 | 5 | 5 |
| 3 | 5 | 5 | 5 | 5 | 5 |
| 4 | 5 | 5 | 5 | 5 | 5 |

TEST EXAMPLE 2 (herbicidal effect test by upland field soil treatment)

In a plastic pot filled with upland field soil (surface area: 120 cm$^2$), seeds of barnyardgrass (Ec), crabgrass (Di), pale smartweed (Po), slender amaranth (Am), and lambsquarters (Ch) were sown to a depth of 0.5 to 1 cm and covered with soil. Next day, a predetermined amount of a wettable powder prepared in accordance with Formulation Example 1 was diluted with water and applied uniformly to the soil surface by a small-sized sprayer in an amount of 100 l/10 ares so that the dose of the active ingredient was 400 g/10 ares. The pot was then cultured in a green house, and the evaluation was conducted on the 21st day after the treatment in accordance with the standard as identified in the above Table 2-1. The test results are shown in the following Table 4.

TABLE 4

| Compound No. | Herbicidal effect | | | | |
|---|---|---|---|---|---|
| | Ec | Di | Po | Am | Ch |
| 1 | 5 | 5 | 5 | 5 | 5 |
| 2 | 5 | 5 | 5 | 5 | 5 |
| 3 | 5 | 5 | 5 | 5 | 5 |
| 4 | 5 | 5 | 5 | 5 | 5 |

TEST EXAMPLE 3 (crop selectivity test by upland field foliage treatment)

In a plastic pot (surface area: 600 cm$^2$) filled with upland field soil, rice (Or), wheat (Tr), corn (Ze), barnyardgrass (Ec), johnsongrass (So), water foxtail (Al), pale smartweed (Po), slender amaranth (Am) and common cocklebur (Xa) were sown to a depth of 0.5 to 1 cm and were cultured in a green house for 2 weeks. A predetermined amount (active ingredient, g/10 ares) of a wettable powder prepared in accordance with Formulation Example 1 was diluted with water, and applied onto the foliage by a small-sized sprayer. The plants were then cultured in the green house, and the evaluations of the herbicidal effect and phytotoxicity were conducted on the 14th day after the treatment in accordance with the standard as identified in the above Tables 2-1 and 2-2. The results are shown in the following Table 5.

TABLE 5

| Compound No. | Dose (active ingredient, g/10 ares) | Herbicidal Effect | | | | | | Phytotoxicity | | |
|---|---|---|---|---|---|---|---|---|---|---|
| | | Ec | So | Al | Po | Am | Xa | Or | Tr | Ze |
| 1 | 1.6 | 5 | 5 | 5 | 5 | 5 | 5 | 0 | 1 | 2 |
| 2 | 1.6 | 5 | 5 | 5 | 5 | 5 | 5 | 0 | — | 1 |
| 3 | 6.3 | 5 | 5 | 5 | 5 | 5 | 5 | 1 | 1 | — |

TEST EXAMPLE 4 (crop selectivity test by paddy field soil treatment)

In a plastic pot (surface area: 1/10,000 are) filled with paddy field soil, barnyardgrass (Ec), monochoria (Mo) and bulrush (Sc) were sown to a depth of 0.5 cm after irrigating, puddling and leveling. In the pot, two pieces of paddy rice (Or) of 2.5 leaf stage were transplanted to a transplanting depth of 2 cm, and flooded to a water depth of 3 cm. Next day, a predetermined amount (active ingredient, g/10 ares) of a wettable powder prepared in accordance with Formulation Example 1 diluted with water, and applied dropwise to the water surface. The plants were then cultured in a green house, and the evaluations of the herbicidal effect and phytotoxicity were conducted on the 28th day after the treatment in accordance with the standards as identified in Tables 2-1 and 2-2. The results are shown in the following Table 6.

The following compounds were used as comparative herbicides.

Comparative Compound 1

Methylthioethyl 2,6-bis(4,6-dimethoxypyrimidin-2-yl)oxybenzoate

Comparative Compound 2

Ethylthioethyl 2,6-bis(4,6-dimethoxypyrimidin-2-yl)oxybenzoate (Both compounds are disclosed in Japanese Unexamined Patent Publication No. 250365/1989.)

TABLE 6

| Compound No. | Dose (active ingredient, g/10 ares) | Herbicidal effect | | | Phytotoxicity |
|---|---|---|---|---|---|
| | | Ec | Mo | Sc | Or |
| 1 | 6.3 | 5 | 5 | 5 | 2 |
| 2 | 6.3 | 5 | 5 | 5 | 1 |
| 3 | 6.3 | 4 | 5 | 5 | 1 |
| Comparative Compound No. 1 | 25.0 | 0 | 3 | 0 | 0 |
| Comparative Compound No. 2 | 25.0 | 0 | 3 | 0 | 0 |

What is claimed is:

1. A pyrimidine derivative having the formula,

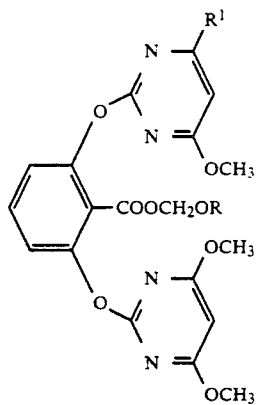

wherein R is a lower alkyl group, and $R^1$ is a lower alkoxy group, a halogen atom or a halogen-substituted lower alkoxy group.

2. The pyrimidine derivative according to claim 1, wherein R is a methyl group or an ethyl group.

3. The pyrimidine derivative according to claim 1, wherein $R^1$ is a lower alkoxy group.

4. The pyrimidine derivative according to claim 3, wherein $R^1$ is a methoxy group.

5. The pyrimidine derivative according to claim 1, wherein R is a methyl group or an ethyl group, and $R^1$ is a methoxy group.

6. The pyrimidine derivative according to claim 1, wherein R is a methyl group, and $R^1$ is a methoxy group, a difluoromethoxy group or a chlorine atom.

7. The pyrimidine derivative according to claim 1, wherein R is an ethyl group, and $R^1$ is a methoxy group.

8. A herbicidal composition comprising a herbicidally effective amount of the pyrimidine derivative of claim 1 and an agricultural adjuvant.

9. A method for killing weeds, which comprises applying a herbicidally effective amount of the pyrimidine derivative of claim 1 to a locus to be treated.

* * * * *